United States Patent
Liao

(10) Patent No.: US 6,220,102 B1
(45) Date of Patent: Apr. 24, 2001

(54) DIE-SHEAR TEST FIXTURE APPARATUS

(75) Inventor: Kuang-Ho Liao, Taipei (TW)

(73) Assignee: Vanguard International Semiconductor Corporation, Hsin-Chu (TW)

( * ) Notice: Subject to any disclaimer, the term of this patent is extended or adjusted under 35 U.S.C. 154(b) by 0 days.

(21) Appl. No.: 09/389,629

(22) Filed: Sep. 3, 1999

(51) Int. Cl.$^7$ ....................................................... G01N 3/08
(52) U.S. Cl. .............................................................. 73/827
(58) Field of Search ............................ 73/826, 827, 828, 73/830, 831, 823, 838, 150 A

(56) References Cited

U.S. PATENT DOCUMENTS

| | | | |
|---|---|---|---|
| 2,377,869 | * 6/1945 | Elliott | 73/828 |
| 3,702,437 | * 11/1972 | McGrath | 324/766 |
| 4,055,992 | * 11/1977 | Pizzarello | 73/791 |
| 4,555,052 | * 11/1985 | Kurtz et al. | 228/104 |
| 5,591,920 | * 1/1997 | Price et al. | 73/828 |

* cited by examiner

*Primary Examiner*—Max Noori
(74) *Attorney, Agent, or Firm*—George O. Saile; Stephen B. Ackerman

(57) ABSTRACT

A new method and apparatus is provided for obtaining a quantitative reading of the strength of the chip bonding connections and for testing the quality of the bonding that is established between a chip and the chip pad or tapes on which the chip is mounted. The invention makes use of the fact that the lead frame, that is the frame that contains the leads to which the chip is connected, uses a material for the metal interconnects that can be controlled by a magnetic field. A metal alloy is commonly used to fabricate the interconnect leads on the lead frame. The alloy is typically selected based on considerations of thermal stress (between the chip and the chip pad or tapes or equivalent interface on which the chip is mounted) and on considerations of delamination between the lead frame and the encapsulating compound. Ni—Fe is an alloy that is frequently used as the material for the metal interconnects on the lead frame. A magnetic field is applied such that this magnetic field holds the lead frame firmly in place with respect to the fixture plate. The lead frame/die combination is mounted such that the chip faces upwards. The die-shear test can now be performed.

22 Claims, 2 Drawing Sheets

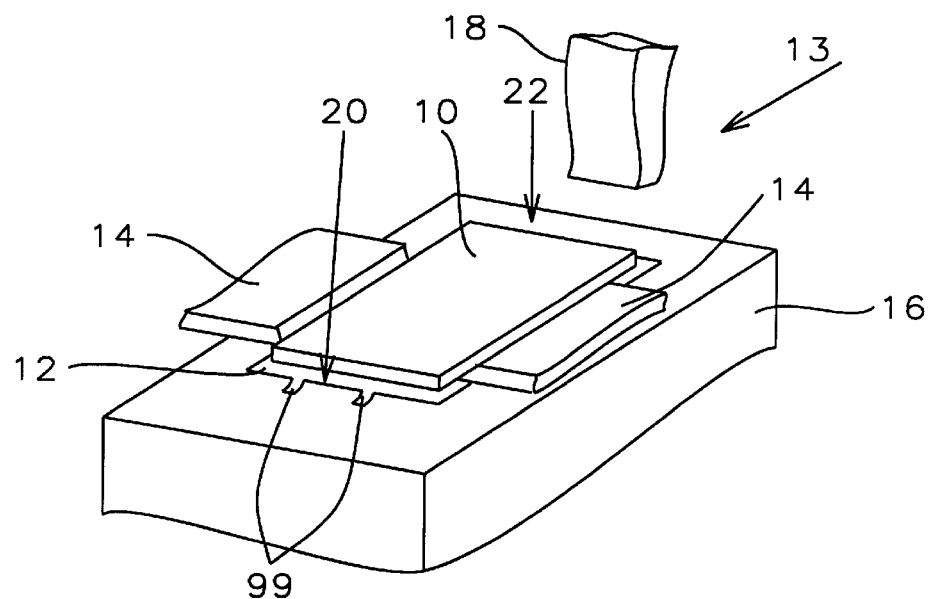
FIG. 1 - Prior Art
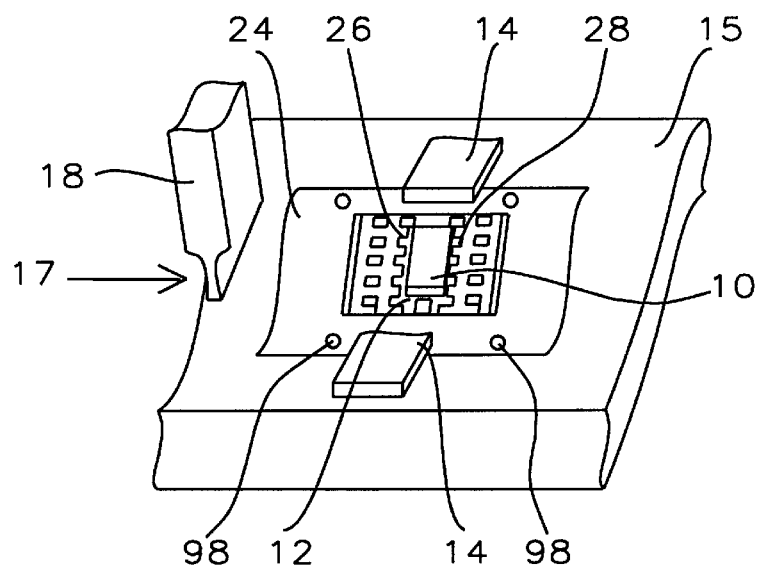
FIG. 2 - Prior Art

DIE-SHEAR TEST FIXTURE APPARATUS

BACKGROUND OF THE INVENTION

(1) Field of the Invention

The invention relates to the fabrication of integrated circuit devices, and more particularly, to a method and apparatus to verify the adequacy or strength of the connection between die bonding and the lead frame during package assembly.

(2) Description of the Prior Art

In the design of semiconductor devices, a large number of metal interconnect lines are created. These interconnect lines can be located in one plane or they can be located on a number of planes that are superimposed within the device package and are part of this package. Contact and via openings are created in the insulating and dielectric layers that separate the interconnect metal structures. Depending on the process design and technology, metal structures can consist of small contact and via openings that range from about 0.3 to 1.0 um. Other metal structures can include wide metal lines ranging from about 1 micrometer to about 20 to 30 micrometer. Or metal bonding pads, which can be as large as about 50 to about 100 um. Bonding pads serve the function of connecting the input and output of the die to other electrical functions such as ground, power and signal functions.

For many of the advanced semiconductor devices, device signals such as ground, power and I/O signals require numerous bonding pads. With the increased density of components within a chip and with increased sophistication of the circuitry contained within the chip, further demands are placed on the number of bonding pads for each chip. For many designs, the number of bonding pads becomes the limiting factor on chip size and chip function.

In the field of semiconductor devices, producing simple, reliable, and inexpensive bonding pads is a primary concern of manufacturing. Bonding pads are wired to device elements located in the semiconductor die substrate and provide exposed contact regions of the die which are suitable for wiring to components external to the die. In one typical case, a bonding wire is attached to the bonding pad at one end and a portion of the lead frame at the other.

An example of a simple and inexpensive bonding pad is an exposed aluminum surface. A gold bonding wire can be bonded to this aluminum pad. An important concern in the creation of such a bonding pad is the pad reliability and its performance under various conditions of temperature. When ambient temperatures are less than approximately 150 degrees C., the physical attachment and the electrical connection between the gold wire and the aluminum pad are sufficiently reliable. However, when temperature rises above 150 degrees C., the bond rapidly degenerates due to the growth of gold and aluminum intermetallics. That is, the two metals start to diffuse between each other and begin forming aluminum-gold chemical compositions. As a result, porosity, delamination, and voiding occur within the bond. Further increasing the temperature tends to worsen this relationship, and the bond will eventually fail. Consequently, potential reliability problems prevent using the aluminum bonding pad under conditions where the ambient temperature is known to exceed 150 degrees C. Furthermore, even when the ambient temperature is less than approximately 150 degrees C., the aluminum bonding pad is susceptible to corrosion simply because it is exposed.

Aluminum can however grow a passivating oxide layer in air and is as a consequence protected against corrosion. Aluminum wiring used in semiconductors, however, contains copper, which does not have a passivating oxide, and the Al—Cu alloy used is more vulnerable to corrosion. The corrosion of aluminum wires is caused by several sources such as chlorine transported through the plastic packaging and the passivation materials, chlorine from the etching compounds and as etching by-products, phosphorous acid formed from excess phosphorous in the phosphosilicate glass, etc. Only a small amount of chlorine is required to cause severe local corrosion of the aluminum lines. Aluminum corrosion can, in addition, occur very quickly after metal etching.

Copper is electro-positive with respect to hydrogen and is not vulnerable to corrosion. However, in air copper oxide grows linearly with time, indicating the lack of a protective oxide. This lack of a passivating oxide makes copper more vulnerable to chemical corrosion. To avoid or minimize this corrosion, most applications of copper metalization involve some protective layer deposited on top of the copper.

A basic requirement for bonding pads is that they provide a maximum number of I/O interconnect locations. Intersection of wires that are used to make these I/O connections is thereby not desired (since these wires would now have to be electrically isolated further adding to the processing cost) which leads to an arrangement for the bonding pads around the periphery of the final package. Materials used for the bonding pads include metallic materials such as tungsten and aluminum while heavily doped polysilicon can also be used for contacting material. The bonding pad is formed on the top surface of the semiconductor device whereby the electrically conducting material is frequently embedded in an insulating layer of dielectric. In using polysilicon as the bonding pad material, polysilicon can be doped with an n-type dopant for contacting N-regions while it can be doped with p-type dopant for contacting P-regions. This approach of doping avoids inter-diffusion of the dopants and dopant migration. It is clear that low contact resistance for the bonding pad area is required while concerns of avoidance of moisture or chemical solvent absorption, thin film adhesion characteristics, delamination and cracking play an important part in the creation of bonding pads. For these reasons extra steps, such as the creation of a metal seed layer and diffusion barrier layers (of Ti or TiN) within the openings created for the deposition of the bonding pad, are often taken if metal (tungsten, aluminum) is used for the bonding pad.

One of the methods than that is used to improve circuit performance and circuit density is to mount semiconductor die in a package or substrate. The interconnects between the die and the substrate are made using die bonding whereby the die-bonds are directly connected to contact points on the package on which the die is mounted. This connection must, for obvious reasons, be dependable and of high quality. This leads to a need for test equipment that accurately tests and measures the bond strength and that can make measurements that relate to and identify the modes of failure that occur when the bonding wire detaches from the bonding pad. Two parameters have thereby been identified, in U.S. Pat. No. 4,055,992, as being relevant and of importance, that is the strength of the connection and the rate of aging of the connection. The bond pull strength is critical in determining both of these factors, the test apparatus must therefore be capable of measuring the force that is required to break the bond and at the same time observe the mode of failure. In view of the fragile nature of semiconductor die, it is difficult to position the die with respect to the test equipment and at the same time make contact with the bond wire while pulling the wire until failure occurs, all the while measuring the force that is being exerted on the wire. Prior Art has provided a number of methods for accomplished this. These Prior Art methods are highlighted below.

An apparatus for testing the bond strength between two laminated layers of material is taught by A. R. Mancini in U.S. Pat. No. 3,019,644. Mancini discloses the use of an electric motor and a force gauge to measure the stripping force of two laminated layers. The apparatus consists of a rigid frame having a common drive shaft connected to several structural elements including sprocket gears, sprocket chain, drive pulleys, idler pulleys, a bifurcated support member, hook and a spring scale. Both layers are slowly advanced by the mechanization in opposite directions until there is a failure; the spring scale measures the force. This type of apparatus is too cumbersome and complex to measure the bond strength of minute beam leads. Also, gripping the beam leads is difficult with a hook.

U.S. Pat. No. 2,377,869 by M. A. Elliott also teaches the use of an electric motor and drive members to test the deep drying properties of insulating materials. This apparatus includes various electrical components that make up a measuring part of the apparatus. The specimen to be tested is held between two clamps. One clamp is suspended from a tension bar. The first clamp is drawn away from the second clamp by a drive motor. The measuring part of the apparatus measures the voltage change with respect to the deflection of the tension bar, which is proportional to the actual tension to which the specimen is subjected. This apparatus is also quite complex, and it is doubtful that it could be adapted to test beam leads.

McGrath, U.S. Pat. No. 3,702,437 discloses a micrometer driver positioning assembly for moving and supporting an electronic assembly during diagnosing and repairing of devices of said electronic assembly. This apparatus lacks a means for clamping the small wires and the micrometer driving assembly does not slide around independently of the micrometer, which is used for fine positioning. Still another apparatus, the "Hunter Terminal Pull Tester" described in Bulletin 750e of Hunter Spring Company, dated September 1961, tests electrical connectors. This apparatus utilizes an air motor having a moving piston, which connects directly to a set of serrated clamping jaws for gripping the wire. An indexing disc provides holding notches for terminals of varying sizes, which is mounted to a force gauge. Once the crimped terminal or connector is secured in the notch on the tension head of the force gate, and the wire is placed between the open jaws of the air motor, the jaws close around the wire and the piston moves at the preset speed. The piston pulls the jaws and wire until the crimped connection fails or the insulation breaks. The force gauge indicates the force exerted to cause the instant failure. While the Hunter tester appears to be adequate for production type terminals, more precise equipment and means is required for securing the minute integrated chips, clamping of the fine beam leads, measuring the beam lead strength and determining the mode of failure.

U.S. Pat. No. 4,055,992 teaches an invention that relates to an apparatus for testing the bond strength of beam leads. The invention utilizes a moving table having X, Y and Z movement. An adjustable probe is attached to the table and has independent vertical and horizontal movement for precisely clamping a beam lead against the table. A mounting bar having a base with an angle of 0 degrees to 90 degrees to the horizontal is used for securing the beam lead chip to the angled surface. The table is moved towards the chip until the table edge is under the beam leads. The probe is then manipulated to clamp a selected beam lead. The mounting bar is connected to a test bar, which is attached to a driving assembly having a force gage. The driving assembly moves the test bar in a circular direction away from the index table until the beam lead breaks the bond from the chip. The force gauge measures the force that caused this failure. A microscope may also be utilized to observe the mode of failure.

In sum, to perform package assembly, die bonding on the lead frame is one of the essential processes. The existing test method, referred to as a die-shear test, verifies the strength of the die-attach to the lead frame. It is a destructive test and measures the force that is needed to push the die away from the lead frame after the die-bonding process has been completed. FIGS. 1 and 2 further detail this method of testing.

In FIG. 1, the chip 10 is mounted on a die pad 12; the die pad 12 is mounted on a lead frame strip (not shown in FIG. 1). The objective of the test as shown in FIG. 1 is to test the adhesion between the die 10 and the die pad 12. Fixture clamp 14 clamps the die pad 12 with the thereon-mounted die 10; the fixture clamp 14 is mounted above the surface of a fixture plate 16 and is supported by this fixture plate 16. Test head 18 is brought into positions 20 or 22 and pushes the die 10 in the direction 13 until the bond between the die 10 and the die pad 12 is broken. It is clear that, before breakage of the bond between the die pad 12 and the chip 10 occurs, a force of significant magnitude is exerted on the chip that is held within the fixture clamp 14, this force may result in mechanical damage to the chip during the test. The fixture clamps 14 are adjustable and can therefore hold the die pad 12 tightly. The clamp 14 can be used to clamp lead frame strips or to clamp single units of a die-pad with the chip mounted.

FIG. 2 shows further detail of the Prior Art test arrangement while the method of clamping the chip is also different. The objective of the test as shown in FIG. 2 is to test the adhesion between the die 10 and the die pad 12 by pushing the die 10 away from the lead frame strip 24. The lead frame strip 24 on which the die pad 12 and the chip 10 are transported is shown in detail. Where in FIG. 1 the die/pad combination was clamped by the fixture clamp, FIG. 2 shows an arrangement where the lead frame strip 24 is clamped to the fixture plate 15 by means of fixture clamps 14. It should be clear from FIG. 2 that the front end of the test head 18, the end that comes in contact with the die 10 during the time that the test is performed, can be positioned along the etches 26 and 28 of the die parallel to the major axis of the fixture clamp 14. A further difference between FIG. 1 and FIG. 2 is the way in which the fixture clamp 14 is mounted with respect to the die pad 12. In FIG. 1, a sample die 10 is mounted on the die pad 12 that has been cut at the tie bar 99 and away from the side-rail 98 (FIG. 2) of the lead frame. FIG. 2 shows an example of the test mechanism with the complete lead frame in tact. It is clear from FIGS. 1 and 2 that, if the separation between the chip and the chip pad occurs in an uneven or random manner, the force exerted on the chip may convert from a linear force (in one direction) to a twisting force (in more than one direction) resulting in a twisting of the chip. This further complicates the Prior Art method of testing by creating bond shear results that are dependent on the position of the test head relative to the die pad. This latter problem is especially acute for Lead On Chip (LOC) type mounting where symmetry of mounting the chip on the die pad is not assured. Present day testing for LOC lead frame requires that the chip gets manually removed from the lead frame (24, FIG. 2), the bottom of the chip is visually inspected to see if tapes or any other adhesive material that have been torn from the lead frame are sticking to the chip and, if the tapes or any other adhesive material are sticking, to conclude that the chip adhesion is good. Chips that are removed in this way and on which the tapes are not sticking are declared failures. For LOC lead frame manufacturing, this method of evaluating bond adhesion does not provide a quantitative reading or a clear insight in the actual quality of the bond that has been established between the chip and the underlying die pad.

SUMMARY OF THE INVENTION

A principle objective of the invention is to provide a quantitative reading method of testing the strength of chip bonding connections.

In accordance with the objectives of the invention a new method and apparatus is provided for obtaining a quantitative reading and for testing the quality of the bonding that is established between a chip and the chip pad on which the chip is mounted. The invention makes use of the fact that the lead frame, that is the frame that contains the leads to which the chip is connected, uses a material for the metal interconnects that can be controlled by a magnetic field. A metal alloy is commonly used to fabricate the interconnect leads on the lead frame. The alloy is typically selected based on considerations of thermal stress (between the chip and the chip pad on which the chip is mounted) and on considerations of delamination between the lead frame and the encapsulating compound. Ni—Fe is an alloy that is frequently used as the material for the metal interconnects on the lead frame. A magnetic field is applied such that this magnetic field holds the lead frame firmly in place with respect to the fixture plate. The lead frame/die combination is mounted such that the chip faces upwards. The die-shear test can now be performed.

BRIEF DESCRIPTION OF THE DRAWINGS

FIG. 1 shows a Prior Art method of performing the die-shear test.

FIG. 2 shows another Prior Art method of performing the die-shear test.

DESCRIPTION OF THE PREFERRED EMBODIMENTS

Figure 3:
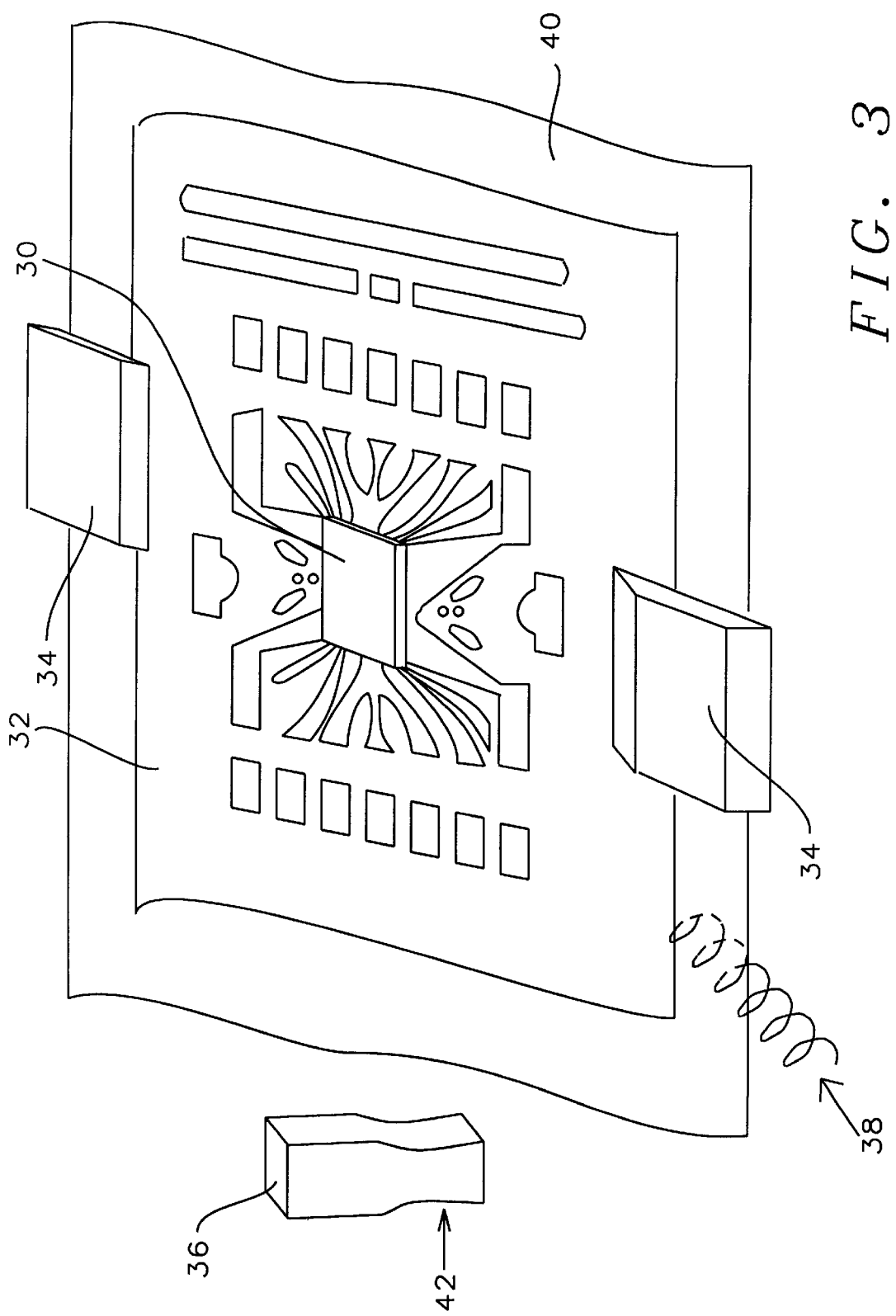
FIG. 3 shows the method of the invention of performing the die-shear test.

Referring now specifically to FIG. 3, there is shown a perspective view of the method and apparatus of the invention to perform the die-shear test. The die 30 is mounted on a LOC lead frame strip 32 that in turn is mounted on the surface of fixture plate 40. The metal used for the metal interconnects of the lead frame strip 32 is a Ni—Fe alloy or any other suitable metal that has magnetic properties similar to Ni—Fe. Underneath the fixture plate 40 is mounted a magnetic coil 38 from which a magnetic field radiates. This magnetic field holds the Ni—Fe lead frame firmly and uniformly in place on the surface of the fixture plate 40 while the die-shear test is being performed. Test head 36 is placed in position around the edges of the chip 30 and force 42 is used to (try to) push the chip 30 from the lead frame strip 32 by pushing the chip in the direction 42. Dependent on the strength of the magnetic field that is supplied by coil 38, the LOC lead frame strip 32 may or may not be further clamped to the fixture plate 40 by means of the clamps 34.

The test that has been described above is meant to be a destructive test because the test is designed to provide a quantitative reading of the test force that needs to be applied in order to remove the die from the beam lead. This test can be performed on a unit that contains only one die (the single die unit) or it can be performed on a unit where multiple chips are mounted on a lead frame strip. With the data that has been obtained in this manner, technical specifications can be established that are used for daily production monitoring of the strength of the chip bonding connections.

Although the invention has been described and illustrated with reference to specific illustrative embodiments thereof, it is not intended that the invention be limited to those illustrative embodiments. Those skilled in the art will recognize that variations and modifications can be made without departing from the spirit of the invention. It is therefore intended to include within the invention all such variations and modifications which fall within the scope of the appended claims and equivalents thereof.

What is claimed is:

1. A method for testing strength or quality of bonding of beam leads that are bonded to a device and of obtaining quantitative readings that are an indication of chip bonding connections, said device being mounted on a lead frame strip or on a single unit, comprising:

clamping said lead frame strip or said single unit by mounting said lead frame strip or said single unit on the surface of a fixture plate, by further mounting a magnetic coil underneath said fixture plate, firmly clamping said lead frame strip or said single unit to said fixture plate, by positioning a clamping arrangement, said clamping arrangement allowing clamping said lead frame strip or said single unit to said fixture plate;

positioning said lead frame strip or said single unit;

exerting pressure on said device; and measuring said pressure.

2. The method of claim 1, said device being a semiconductor device of the Lead On Chip type.

3. The method of claim 1, said single unit comprising a beam lead and a chip.

4. The method of claim 3, said beam leads comprising:

bond points that connect said device to said lead frame strip;

a multiplicity of contact pads distributed around a periphery of said lead frame strip; and a multiplicity of metal interconnect lines interconnecting said bond points with said contact pads, said contact pads forming points for interconnecting said lead frame strip with surrounding circuitry.

5. The method of claim 1, said lead frame strip comprising a multiplicity of said beam leads, furthermore a semiconductor chip being mounted on each beam lead.

6. The method of claim 1 wherein said means for measuring said pressure comprises a strain gauge for sensing change in force that is applied across the strain gauge as a function of said force, yielding an output signal that being converted into a graphical representation indicating said applied force during exertion of said force.

7. The method of claim 1, wherein exerting pressure on said device comprises:

applying force to an edge of said device or chip, said force being perpendicular to said edge of said device and being in a plane of said device, said force being applied by a test head; and applying said force to any side of said device.

8. The method of claim 7 wherein said test head is a probe, whereby said probe:

comprises a tip, said tip having a lower surface;

said lower surface having a rectangular cross section having sides;

one of the sides of said rectangular cross section being used to exert said force on said device; and said probe being provided with independent adjustment means for manipulating said probe in an X, Y and Z direction in addition to rotational freedom of direction.

9. The method of claim 1 wherein said positioning said lead frame strip or said single unit comprises:

linear freedom of movement of said lead frame strip or said single unit in an X, Y, and Z direction;

rotational freedom of movement of said lead frame strip or said single unit;

positioning said lead frame strip or said single unit such that said test head applies force to any side of said device; and maintaining said test head in a stationary position.

10. The method of claim 1 wherein said positioning said lead frame strip or said single unit comprises:

linear freedom of movement of said test head in an X, Y, and Z direction;

rotational freedom of movement of said test head;

positioning said test head such that said test head applies force to any side of said device; and maintaining said lead frame strip or said single unit in a stationary position.

11. The method of claim 1 wherein said means for measuring said pressure comprises a force gauge.

12. An apparatus for testing quality of bonding of beam leads that are bonded to a device, said device being mounted on a lead frame strip or as a single unit, comprising:

a means for clamping said lead frame strip or said single unit, said means for clamping said lead frame strip or said single unit comprising a fixture plate on which is mounted said lead frame strip or said single unit, further comprising a magnetic coil that is mounted underneath said fixture plate firmly clamping said lead frame strip to said fixture plate, further comprising a clamping arrangement, said clamping arrangement allowing for clamping said lead frame strip or said single unit to said fixture plate;

a means for positioning said lead frame strip or said single unit;

a means for exerting pressure on said device; and a means for measuring said pressure.

13. The apparatus of claim 12, wherein said means for measuring said pressure comprises a force gauge.

14. The apparatus of claim 12, wherein said device comprises a semiconductor device of Lead On Chip type.

15. The apparatus of claim 12, said single unit comprising a beam lead and a chip.

16. The apparatus of claim 15, said beam lead comprising:

bond points connecting said device to said lead frame strip;

a multiplicity of contact pads distributed around a periphery of said lead frame strip; and a multiplicity of metal interconnect lines interconnecting said bond points with said contact pads, said contact pads forming points where said lead frame strip being interconnected with surrounding circuitry.

17. The apparatus of claim 12, said lead frame strip comprising a multiplicity of said beam leads, furthermore a semiconductor chip being mounted on each beam lead.

18. The apparatus of claim 12 wherein said means for measuring said pressure comprises a strain gauge for sensing change in force that is applied across the strain gauge as a function of said force, yielding an output signal being converted into a graphical representation indicating said applied force during exertion of said force.

19. The apparatus of claim 12, said means for exerting pressure on said device comprising:

a means for applying force to said semiconductor device or chip, said force being in a plane of said semiconductor device or chip, said force being applied by a test head; and a means for applying said force to any side of said semiconductor device or chip.

20. The apparatus of claim 19 wherein said test head is a probe, said probe comprising:

a tip, said tip having a lower surface;

said lower surface having a rectangular cross section having sides;

one of the sides of said rectangular cross section being used to exert said force on said device; and said probe being provided with independent adjustment means for manipulating said probe in an X, Y and Z direction.

21. The apparatus of claim 12 wherein said means for positioning said lead frame strip or said single unit comprises:

linear freedom of movement of the lead frame strip or a single unit in an X, Y, and Z direction;

rotational freedom of movement of the lead frame strip or said single unit;

means for positioning said lead frame strip or a single unit such that said test head can apply force to any side of said device; and means for maintaining said test head in a stationary position.

22. The apparatus of claim 12 wherein said means for positioning said lead frame strip comprises:

linear freedom of movement of the test head in an X, Y, and Z direction;

rotational freedom of movement of the test head;

means for positioning said test head such that said test head applies force to any side of said device; and means for maintaining said lead frame strip or said single unit in a stationary position.

* * * * *